US008246543B2

(12) United States Patent
Johnson et al.

(10) Patent No.: US 8,246,543 B2
(45) Date of Patent: Aug. 21, 2012

(54) IMAGING METHOD UTILIZING ATTENUATION AND SPEED PARAMETERS IN INVERSE SCATTERING TECHNIQUES

(75) Inventors: Steven A. Johnson, Salt Lake City, UT (US); David T. Borup, Salt Lake City, UT (US); James W. Wiskin, Salt Lake City, UT (US)

(73) Assignee: CVUS Clinical Trials, LLC, Salt Lake City, UT (US)

( * ) Notice: Subject to any disclaimer, the term of this patent is extended or adjusted under 35 U.S.C. 154(b) by 1028 days.

(21) Appl. No.: 12/152,637

(22) Filed: May 14, 2008

(65) Prior Publication Data

US 2008/0294043 A1    Nov. 27, 2008

Related U.S. Application Data

(60) Provisional application No. 60/930,413, filed on May 15, 2007, provisional application No. 60/930,377, filed on May 15, 2007.

(51) Int. Cl.
*A61B 8/00* (2006.01)
*G06K 9/20* (2006.01)
(52) U.S. Cl. .................. 600/442; 600/437; 382/131
(58) Field of Classification Search .................. None
See application file for complete search history.

(56) References Cited

U.S. PATENT DOCUMENTS

| 3,765,403 A | 10/1973 | Brenden |
| 3,805,596 A | 4/1974 | Klahr |
| 3,885,224 A | 5/1975 | Klahr |
| 3,963,933 A | 6/1976 | Henkes |
| 4,047,520 A | 9/1977 | Soldner et al. |
| 4,074,564 A | 2/1978 | Andersen |

(Continued)

FOREIGN PATENT DOCUMENTS

WO    WO 2004/091369    10/2004

OTHER PUBLICATIONS

MacDonald, Calum et al., "Nonlinear Seismic Inversion", Abstract of presentation made at 54th Annual Meeting and Exposition of the Society of exploration Geophysicists at Atlanta, Ga., Dec. 2-6, 1984, pp. 655-657.

(Continued)

*Primary Examiner* — Long V. Le
*Assistant Examiner* — Angela M Hoffa
(74) *Attorney, Agent, or Firm* — Thorpe North & Western LLP

(57) ABSTRACT

Methods for imaging the internal structures of an object using an acoustic wave field are provided. In one aspect, for example, a method of imaging internals of a physical object using acoustic waves may include transmitting an acoustic wave field toward the object, receiving a resultant acoustic wave field with a receiver, where the resultant acoustic wave field is in response to the transmitted acoustic wave field reflected from or transmitted through the object, and determining a predicted resultant acoustic wave field derived from a model of the object. The method may also include determining a residual between the predicted resultant acoustic wave field and the resultant acoustic wave field, and back propagating the residual to determine corrections to the model of the object. In another aspect, the above recited steps may be further iterated to successively refine the model of the object over a number of iterations until a predefined condition is reached.

53 Claims, 4 Drawing Sheets

U.S. PATENT DOCUMENTS

| | | | |
|---|---|---|---|
| 4,075,883 | A | 2/1978 | Glover |
| 4,100,916 | A | 7/1978 | King |
| 4,105,018 | A | 8/1978 | Greenleaf et al. |
| 4,109,642 | A | 8/1978 | Reid et al. |
| 4,109,644 | A | 8/1978 | Kojima |
| 4,120,291 | A | 10/1978 | Paton et al. |
| 4,222,274 | A | 9/1980 | Johnson |
| 4,252,125 | A | 2/1981 | Linuma |
| 4,282,880 | A | 8/1981 | Gardineer et al. |
| 4,298,009 | A | 11/1981 | Mezrich et al. |
| 4,317,369 | A | 3/1982 | Johnson |
| 4,328,707 | A | 5/1982 | Clement et al. |
| 4,341,222 | A | 7/1982 | Gardineer et al. |
| 4,433,690 | A | 2/1984 | Green et al. |
| 4,485,819 | A | 12/1984 | Igl |
| 4,509,368 | A | 4/1985 | Whiting et al. |
| 4,594,662 | A | 6/1986 | Devaney |
| 4,662,222 | A * | 5/1987 | Johnson .................... 73/602 |
| 4,727,550 | A | 2/1988 | Chang et al. |
| 4,798,209 | A | 1/1989 | Klingenbeck et al. |
| 5,078,142 | A | 1/1992 | Siczek |
| 5,227,797 | A | 7/1993 | Murphy |
| 5,305,757 | A | 4/1994 | Unger et al. |
| 5,339,815 | A | 8/1994 | Liu et al. |
| 5,474,072 | A | 12/1995 | Shmulewitz |
| 5,588,032 | A | 12/1996 | Johnson et al. |
| 5,609,152 | A | 3/1997 | Pellegrino et al. |
| 5,667,893 | A | 9/1997 | Kinzer et al. |
| 5,696,848 | A * | 12/1997 | Patti et al. ................. 382/254 |
| 5,806,521 | A | 9/1998 | Morimoto et al. |
| 5,833,633 | A | 11/1998 | Sarvazyan |
| 5,999,836 | A | 12/1999 | Nelson et al. |
| 6,005,916 | A | 12/1999 | Johnson et al. |
| 6,019,724 | A | 2/2000 | Gronningsaeter et al. |
| 6,027,447 | A | 2/2000 | Li |
| 6,304,770 | B1 | 10/2001 | Lee et al. |
| 6,409,668 | B1 | 6/2002 | Wollschlaeger |
| 6,419,390 | B1 | 7/2002 | Landis-Lowell |
| 6,478,739 | B1 | 11/2002 | Hong |
| 6,480,565 | B1 | 11/2002 | Ning |
| 6,483,891 | B1 | 11/2002 | Lazarev et al. |
| 6,587,540 | B1 | 7/2003 | Johnson et al. |
| 6,587,590 | B1 | 7/2003 | Pan |
| 6,636,584 | B2 | 10/2003 | Johnson et al. |
| 6,693,558 | B2 | 2/2004 | Hedrick |
| 7,094,205 | B2 | 8/2006 | Marmarelis |
| 7,264,592 | B2 | 9/2007 | Shehada |
| 7,480,574 | B2 * | 1/2009 | Dubois et al. ................... 702/39 |
| 7,551,708 | B2 * | 6/2009 | Basu et al. ................... 378/5 |
| 7,570,742 | B2 * | 8/2009 | Johnson et al. ............... 600/309 |
| 7,684,846 | B2 * | 3/2010 | Johnson et al. ............... 600/407 |
| 7,699,783 | B2 | 4/2010 | Hanover et al. |
| 7,771,360 | B2 | 8/2010 | Johnson et al. |
| 7,841,982 | B2 * | 11/2010 | Johnson et al. ............... 600/437 |
| 2002/0065461 | A1 | 5/2002 | Cosman |
| 2002/0131551 | A1 | 9/2002 | Johnson et al. |
| 2004/0034307 | A1 * | 2/2004 | Johnson et al. ............... 600/459 |
| 2004/0064046 | A1 | 4/2004 | Shehada |
| 2004/0082856 | A1 | 4/2004 | Marmarelis |
| 2005/0143638 | A1 | 6/2005 | Johnson et al. |
| 2006/0009693 | A1 | 1/2006 | Hanover et al. |
| 2006/0009696 | A1 | 1/2006 | Hanover et al. |
| 2006/0084859 | A1 * | 4/2006 | Johnson et al. ............... 600/407 |
| 2006/0173304 | A1 | 8/2006 | Wang |
| 2006/0287596 | A1 * | 12/2006 | Johnson et al. ............... 600/437 |
| 2006/0293597 | A1 * | 12/2006 | Johnson et al. ............... 600/437 |
| 2007/0282200 | A1 * | 12/2007 | Johnson et al. ............... 600/437 |

OTHER PUBLICATIONS

P.R. Williamson, "Tomographic inversion in reflection seismology," Geophys. J. Int. 100, pp. 255-274, 1990.

W.W. Kim et al., Accelerated Inverse Scattering Algorithms for Higher Contrast Objects, in 1987 IEEE Ultrasonics Symposium, 903-906, (IEEE Cat. No. 87ch2492-7).

S.J. Norton, "Iterative Seismic Inversion," Geophysical Journal, No. 94, pp. 457-468 (1988).

T.K. Sarkar, et al., (1986) "Application of FFT and the Conjugate Gradient Method for the Solution of Electromagnetic Radiation from Electrically Large and Small Conducting Bodies," IEEE Trans. Antennas Propagat., vol. AP-34, pp. 635-640, May.

R.J. Wombell and M.A. Fiddy (1988), "Inverse Scattering Within the Distorted-wave Born Approximation," Inverse Problems 4 (1988).

Y. Zhou et al., "Constrained Reconstruction of Object Acoustic Parameters from Noisy Ultrasound Scattering Data," Proc. of the IEEE 1987 Ultrasonics Symposium pp. 897-901 (1987).

Kostas T. Ladas and A. J. Devaney, "Iterative Methods in Geophysical Diffraction Tomography," Inverse Problems 8 (1992).

M.J. Berggren, et al., "Acoustic Inverse Scattering Images from Simulated Higher Contrast Objects and from Laboratory Test Objects," Acoustical Imaging 16, Chicago, Illinois, Jun. 1987.

Brent S. Robinson and James F. Greenleaf, "An Experimental Study of Diffraction Tomography Under the Born Approximation," Acoustical Imaging vol. 18, 1991. pp. 391-400.

W.W. Kim et al., "Analysis of Inverse Scattering Solutions from Single Frequency, Combined Transmission and Reflection Data for the Helmholtz and Riccati Exact Wave Equations," Acoustical Imaging 15, pp. 359-369, Plenum Press (1987).

E.J. Ayme-Bellegarda et al., "Forward Ultrasonic Scattering from Multidimensional Solid or Fluids Inclusions Buried in Multilayered Elastic Structures," IEEE Trans. Ultras., Ferro., and Freq. Cont., vol. 39, No. 1, Jan. 1992.

E.J. Ayme-Bellegarda and T.M. Habashy, "Ultrasonic Inverse Scattering of Multidimensional Objects Buried in Multilayered Elastic Background Structures," IEEE Transactions on Ultrasonics, Ferroelectics, and Frequency Control, vol. 39, No. 1, Jan. 1992.

J.K. Cohen and F.G. Hagin, "Velocity Inversion Using a Stratified Reference," Geophysics, vol. 50, 11, 1985 pp. 1689-1700.

E. Crase et al., "Robust Elastic Nonlinear Waveform Inversion: Application to Real Data," Geophysics, vol. 55, No. 5 (May 1990) pp. 527-538.

Peter Mora, "Nonlinear Two-dimensional Elastic Inversion of Multioffset Seismic Data," Geophysics, vol. 52, No. 9, Sep. 1987.

G.S. Pan et al., "Full-waveform Inversion of Plane-wave Seismograms in Stratified Acoustic Media: Theory and Feasibility," Geophysics, vol. 53, No. 1 (1988). pp. 21-31.

G.R. Franssens, "Calculation of the Elasto-dynamic Green's Function in Layered Media by Means of a Modified Propagator Matrix Method," Geophys. J.R. astr. Soc. 1983 75, pp. 669-691.

B.L.N. Kennett and N.J. Kerry, "Seismic Waves in a Stratified Half Space," Geophys. J.R. astr. Soc. 57, pp. 557-583, 1979.

Lines, Larry R. et al., "Inversion with a Grain of Salt," Abstract of presentation made at 54th Annual Meeting and Exposition of the Society of Exploration Geophysicists at Atlanta, Ga., Dec. 2-6, 1984, pp. 638-640.

Johnson, S.A. et al., (1984) "Inverse Scattering Solutions by a Sinc Basis. Multiple Source Moment Method—Part III: Fast Algorithms." Ultrasonic Imaging 6, pp. 103-116.

Johnson S.A. et al., (1983) "Inverse Scattering Solutions by a Sinc Basis, Multiple Source, Moment Method—Part I: Theory." Ultrasonic Imaging 5, 361-375.

Johnson, S.A. et al., (1983) "Acoustical Inverse Scattering Solutions by Moment Methods and Backpropagation." in Conference on Inverse Scattering: Theory and Application. SIAM, Philadelphia. pp. 144-155.

La Bras, L. et al., "Presentation of a Born Inversion for Multioffset Reflection Data: Tests on Synthetic Seismograms," Abstract of presentation made at 54th Annual Meeting and Exposition of the Society of Exploration Geophysicists at Atlanta, Ga., Dec. 2-6, 1984.

Kaman, E. J., "Detailed Inversion of Reservoir Data by Constrained Parameter Estimation and Resolution Analysis," Abstract of presentation made at 54th Annual Meeting and Exposition of the Society of Exploration Geophysicists at Atlanta, Ga., Dec. 2-6, 1984. pp. 652-655.

Johnson, Steven A. et al., "Ultrasound Tomography by Galerkin or Moment Methods", Lecture Notes in Medical Informatics, (1984) vol. 23, pp. 254-276.

Tarantola, A. et al., "Inverse Problems: Quest of Information", J. Geophysics, vol. 50, No. 3, pp. 159-170 (1982).

Verwest, B. J. et al., "Prestack Inversion of Plane-Layered Viscoacoustic Earth Parameters," Abstract of presentation at 54th Annual Meeting and Exposition of the Society of the Exploration Geophysicist at Atlanta, Ga., Dec. 2-6, 1984.

Carrion, Philip M. et al., A Method for Computation of Velocity Profiles by Inversion of Large-Offset Records; Geophysics, (1984) pp. 1249-1258 vol. 49, No. 8.

Tarantola, A., "Linearized Inversion of Seismic Reflection Data," Geophysical Prospecting, vol. 32, pp. 998-1015 (1984).

De Figueiredo, Rui J.P., "Approximation-Theoretic Methods for Nonlinear Deconvolution and Inversion", Information Sciences, pp. 209-220 (1983) vol. 31, No. 3.

Tarantola, Albert et al., "Nonlinear Inversion of Seismic Reflection Data", Abstract of presentation made at the 54th Annual Meeting & Exposition of the Society of Exploration Geophysicists held at Atlanta, Dec. 2-6, 1984, pp. 645-658.

Goutsias et al., "A 2-D Stochastic Earth Model for Seismic Inversion", Abstract of presentation made at the 54th Annual Meeting and Exposition of the Society of Exploration Geophysicists held at Atlanta, Ga., Dec. 2-6, 1984, pp. 385-386.

Greenleaf, James F., edited by D. W. McLaughlin Computer Tomography from Ultrasound Scattered by Biological Tissues, SIAM-AMS Proceedings (1984) pp. 53-63.

Hanson, Douglas W., "Multiparameter Seismic Inversion of Noisy Data", Abstract of presentation made at the 54th Annual Meeting and Exposition of the Society of Exploration Geophysicists held at Atlanta, Ga., Dec. 2-6, 1984.

Harkrider, David G., "Synthetics and Theoretical Seismology", Reviews of Geophysics and Space Physics, (1983) vol. 21, No. 6, pp. 1299-1308.

McClary, W. Keith, "Fast Seismic Inversion", Geophysics, (1983) vol. 48, No. 10, pp. 1371-1372.

Morley, Lawrence C., "Invertibility of Elastic Layered Earth Parameters from Precritical P-Wave Reflection Amplitudes", Abstract of presentation at 54th Annual Meeting and Exposition of the Society of Exploration Geophysicists at Atlanta, Ga., Dec. 2-6, 1984, pp. 641-643.

Nercessian, A., "Linearized Inversion of Multioffset Seismic Reflection Data," Abstract of presentation at 54th Annual Meeting and Exposition of the Society of Exploration Geophysicists at Atlanta, Ga., Dec. 2-6, 1984.

P. D. Corl et al., "A Digital Synthetic Focus Acoustic Imaging System", Acoustical Imaging, 8th Int'l. Conference, Jun. 1978, pp. 39-53.

S. A. Johnson et al., High Resolution Ultrasound Echo and Reconstruction Imaging from Temporal and Spatial Projections by Adaptive Ray Tracing, Proceedings of the 4th International Joint Conference Pattern Recognition, Feb. 1978 pp. 846-850.

S. A. Johnson et al., Quantitative Synthetic Aperture Reflection Imaging Correction for Refraction and Attenuation: Appl. Seismic Tech. in Medicine, Feb. 1978, pp. 337-349.

S. A. Johnson et al., Ultrasound Images Corrected for Refraction and Attenuation: Comparison of New High Resolution Methods, Aug. 1979, pp. 55-71.

S. A. Johnson, et al., "Algebraic and Anly. Inversion Acou. Data Partially or Fully Enclosing Apertures", Acoustical Imaging, pp. 577-598, Jun. 1978.

Sigalov, Ya. B. et al., "On the Solution of the Two-Dimensional Inverse Dynamic Problem of Seismometry by the Finite-Difference Method, Part 1." Geophysical Journal, vol. 5, No. 4, pp. 508-521 (1984).

Tarantola, A. et al., "Generalized Nonlinear Inverse Problems Solved Using the Lease Squares Criterion," Review of Geophysics and Space Physics, vol. 20, No. 2, pp. 219-232 (1982).

Tarantola, A., "Inversion of Seismic Reflection Data in the Acoustic Approximation", Geophysics, vol. 49, No. 8, pp. 1259-1266 (1984).

U.S. Appl. No. 12/152,631, filed May 14, 2008; Steven A. Johnson; office action issued Dec. 20, 2011.

* cited by examiner

IMAGING METHOD UTILIZING ATTENUATION AND SPEED PARAMETERS IN INVERSE SCATTERING TECHNIQUES

PRIORITY DATA

This application claims the benefit of U.S. Provisional Patent Application Ser. Nos. 60/930,413 and 60/930,377, both filed on May 15, 2007, and both of which are incorporated herein by reference in their entireties.

BACKGROUND OF THE INVENTION

1. Field of the Invention

The present invention relates generally to acoustic imaging systems.

2. Related Art

Various imaging techniques for imaging inside objects are known. For example, x-ray and magnetic resonance imaging has found use as a medical diagnosis tool. It is also known that acoustic waves can be propagated through objects. When an acoustic wave propagates through a non-homogenous object, it is affected by spatial variations in the stiffness, density and absorption of the object. Non-uniformities can result in attenuation, varying propagation speed, reflection, refraction, and scattering of the acoustic waves passing through the object. By transmitting an acoustic wave into the object, and measuring the resulting affect on the acoustic wave by the object, it is possible to construct an image of the internal structures of the object. This image construction process is sometimes called "inverse scattering."

While many advances in image imaging have been provided over the years, solutions to specific problems have achieved varying success. For example, the present inventors have been developing the technique of ultrasound computed tomography for several years. Ultrasound computed tomography may enable imaging structures within the human breast to allow diagnosis of diseases, such as breast cancer.

Other than skin cancer, breast cancer is the most common cancer among women, and is the second leading cause of cancer death in women, after lung cancer. Approximately 44.5 million women in the United States are screened for breast cancer each year with 10% or 4.5 million referred for a second diagnostic test. The American Cancer Society Breast Cancer Statistics report indicates that 1 in 7 women will get breast cancer during her lifetime. The current standard of care has significant problems, generating unacceptably high rates of false positive tests—between 8% and 10%—and upwards of 15% false negative tests. The result is that many women suffer from unnecessary and invasive biopsies. In addition, each year the U.S. healthcare system spends an estimated $2.1 billion on biopsies, which yield negative results more than 75% of the time.

Breast cancer is a malignant tumor that has developed from cells of the breast. A malignant tumor is a group of cancer cells that may invade surrounding tissues or spread (metastasize) to distant areas of the body. The female breast is made up mainly of lobules (milk-producing glands), ducts (milk passages that connect the lobules to the nipple), and stroma (fatty tissue and connective tissue surrounding the ducts and lobules, blood vessels, and lymphatic vessels). Lymphatic vessels are like veins, except that they carry lymph instead of blood. Lymph is a clear fluid that contains tissue waste products and immune system cells (cells that are important in fighting infections). Lymph nodes are small bean-shaped collections of immune system cells that are found along lymphatic vessels. Cancer cells can enter lymphatic vessels and spread to lymph nodes. Most lymphatic vessels in the breast connect to lymph nodes under the arm (axillary lymph nodes). Some lymphatic vessels connect to lymph nodes inside the chest (internal mammary nodes) and either above or below the collarbone (supra- or infra-clavicular nodes). When breast cancer cells reach the axillary (underarm) lymph nodes, they may continue to grow, often causing the lymph nodes in that area to swell. If breast cancer cells have spread to the underarm lymph nodes, they are more likely to have spread to other organs of the body as well. Thus, it is important to find out if breast cancer has spread to the axillary lymph nodes when choosing a treatment.

Most breast lumps are not cancerous, that is, they are benign. Most lumps turn out to be fibrocystic changes. The term "fibrocystic" refers to fibrosis and cysts. Fibrosis is the formation of fibrous (or scar-like) connective tissue, and cysts are fluid-filled sacs. Fibrocystic changes can cause breast swelling and pain. This often happens just before a period is about to begin. The breast may feel nodular, or lumpy, and, sometimes, a clear or slightly cloudy nipple discharge is noticed. Benign breast tumors such as fibroadenomas or papillomas are abnormal growths, but they are not cancer and cannot spread outside of the breast to other organs.

Although widespread use of screening mammography has increased the number of breast cancers found before they cause any symptoms, some breast cancers are not found by mammography, either because the test was not done or because even under ideal conditions mammography cannot find every breast cancer. The most common sign of breast cancer is a new lump or mass. A painless, hard mass that has irregular edges is more likely to be cancerous, but some rare cancers are tender, soft, and rounded. An elliptical mass with its major axis perpendicular to skin line or to natural internal tissue planes (or penetrating such planes), is a danger signal that requires further investigation. For this reason, it is important that a health care professional who is experienced in diagnosing breast diseases check any new breast mass or lump.

Other signs of breast cancer include a generalized swelling of part of a breast (even if no distinct lump is felt), skin irritation or dimpling, nipple pain or retraction (turning inward), redness or scaliness of the nipple or breast skin, or a discharge other than breast milk. Sometimes a breast cancer can spread to underarm lymph nodes even before the original tumor in the breast tissue is large enough to be felt.

If there is any reason to suspect breast cancer, other tests should be performed. After a complete physical exam (including a clinical breast exam), doctors often recommend a diagnostic mammogram or a breast ultrasound. A clinical breast examination (CBE) is an exam of the breasts by a health professional, such as a doctor, nurse practitioner, nurse, or physician assistant. The examiner first looks at the breasts for changes in size or shape. Then, using the pads of the finger tips, the breasts are felt for lumps.

Although mammograms are mostly used for screening, they can also be used to examine a breast of a woman who has a breast problem. This can be a breast mass, nipple discharge, or an abnormality that was found on a screening mammogram. In some cases, special images known as cone views (or spot views) with magnification are used to increase contrast and thus make a small area of altered breast tissue easier to evaluate. A diagnostic mammogram may show that a lesion (area of abnormal tissue) has a high likelihood of being benign (not cancer). In these cases, it is common to ask the woman to come back sooner than usual for a recheck, usually in 4 to 6 months. On the other hand, a diagnostic mammogram may show that the abnormality is not worrisome at all, and the woman can then return to having routine yearly mammograms. Finally, the diagnostic work-up may suggest that a biopsy is needed to tell if the lesion is cancer.

Ultrasound, also known as sonography, uses high-frequency sound waves to outline a part of the body and to visualize internal organs and tissue. High-frequency sound waves are transmitted into the area of the body being studied and echoed back. A computer or dedicated electronic circuitry picks up the sound wave echoes and changes them into an image that is displayed on a computer screen. Breast ultrasound is sometimes used to evaluate breast abnormalities that are found during mammography or a physical exam. One of the most common abnormalities that women have is fibrocystic disease. Ultrasound is useful for detecting fibrocystic disease. It is the easiest way to tell if a cyst is present without placing a needle into it to draw out fluid. It can also find some breast masses. Conventional medical ultrasound uses a single ultrasound array to both transmit and receive echoes and thereby measure the ultrasound reflectivity and distance of various objects under the skin surface. It assumes that the speed of sound is constant through the tissue being imaged. It has difficulty imaging objects with low reflectivity or high absorption of sound. It produces images which are typically two-dimensional, distorted, grainy, and contain speckle. Foreground objects tend to mask deeper structures (e.g. cast shadows on).

A biopsy is done when mammograms, ultrasound, or the physical examination finds a tumor. A biopsy is the only way to tell if cancer is really present. All biopsy procedures remove a tissue sample for examination under a microscope. There are several types of biopsies, such as fine needle aspiration biopsy, core (large needle) biopsy, and surgical biopsy. Biopsies are often done under ultrasound or MRI guidance. Each type of biopsy has distinct advantages and disadvantages. The choice of which to use will depend on the specific situation. Some of the factors the doctor will consider include how suspicious the lesion appears, how large it is, where in the breast it is located, how many lesions are present, other medical problems the patient may have, and the patient's personal preferences. Statistically, three of four biopsies are benign.

SUMMARY OF THE INVENTION

The present invention provides techniques for imaging the internal structures of an object using an acoustic wave field. In one aspect, for example, a method of imaging internals of a physical object using acoustic waves may include transmitting an acoustic wave field toward the object, receiving a resultant acoustic wave field with a receiver, where the resultant acoustic wave field is in response to the transmitted acoustic wave field reflected from or transmitted through the object, and determining a predicted resultant acoustic wave field derived from a model of the object. The method may also include determining a residual between the predicted resultant acoustic wave field and the resultant acoustic wave field, and back propagating the residual to determine corrections to the model of the object. In another aspect, the above recited steps may be further iterated to successively refine the model of the object over a number of iterations until a predefined condition is reached. Additionally, numerous objects are contemplated that can be imaged using the techniques according to aspects of the present invention. In one aspect, however, the object may be a body part. In a more specific aspect, the object may be a human breast.

Various techniques for initializing the model of the object are possible, all of which are considered to be within the scope of the claims. In one aspect, however, the model may be initialized based on a resultant acoustic wave field transmitted through the object. In a more specific aspect, initializing the model of the object may include defining a plurality of points on a computation grid to represent the object, and initializing a speed parameter associated with each of the plurality of points based on transmission time delay between the acoustic wave field and the resultant acoustic wave field. In another specific aspect, initializing the model of the object may include defining a plurality of points on a computation grid to represent the object, and initializing an attenuation parameter associated with each of the plurality of points based on attenuation between the acoustic wave field and the resultant acoustic wave field. In another aspect, however, the model may be initialized based on a resultant acoustic wave field reflected from the object. In a more specific example, initializing the model of the object may include defining a plurality of points on a computation grid to represent the object, and initializing a speed parameter associated with each of the plurality of points based on echo time delay between the acoustic wave field and the resultant acoustic wave field.

In another aspect of the present invention, the model of the object may include a plurality of points on a computational grid. In one specific aspect, each of the plurality of points includes a speed parameter to thus define a speed image. In another specific aspect, each of the plurality of points includes an attenuation parameter to thus define an attenuation image. In yet another aspect, each of the plurality of points includes a speed parameter to define a speed image and an attenuation parameter to define an attenuation image. It may be useful in such cases to back propagate the residual to determine corrections to the model of the object by holding the speed parameters constant while updating the attenuation parameters. Alternatively, back propagating the residual to determine corrections to the model of the object may also be accomplished by holding the attenuation parameters constant while updating the speed parameters.

The computational grids according to various aspects of the present invention are contemplated to be in a variety of configurations. For example, in one aspect the computational grid may include a rectangular arrangement of the plurality of points. In another aspect, the computational grid may include a rectangular arrangement of the plurality of points in a two-dimensional plane. In yet another aspect, the computational grid may include a rectangular arrangement of the plurality of points in a three-dimensional space. In a further aspect, the resolution of the computational grid varies as a function of the acoustic wave frequency.

In another aspect of the present invention, the method may further include determining an incident wave field when the object is not present, and dividing the resultant acoustic wave field by the incident wave field. In a more specific aspect, determining the incident wave field further includes transmitting an acoustic wave field toward the receiver when the object is not present, and receiving an incident acoustic wave field at the receiver in response to the acoustic wave field. In another more specific aspect, determining an incident wave field further includes predicting an incident acoustic wave field received at the receiver in response to the acoustic wave field when the object is not present.

A variety of methods are contemplated to reduce the dynamic range between portions of the resultant acoustic wave field that pass through the object and portions of the resultant acoustic wave field that do not pass through the object, or that pass through portions of the object that have a reduced thickness. In one aspect, for example, the acoustic wave field may be tailored to reduce field intensity in directions where the acoustic wave field does not pass through the object before reaching the receiver relative to field intensity in directions where the acoustic wave field does pass through the object before reaching the receiver. In another aspect, tailoring the acoustic wave field can further include tailoring the acoustic wave field to reduce field intensity in directions where the acoustic wave field passes through portions of the object having decreased tissue thickness relative to portions of the object having increased tissue thickness. In yet another aspect, tailoring the acoustic wave field may further include tailoring the acoustic wave field to reduce field intensity in directions where the acoustic wave field passes through portions of the object having reduced density relative to portions of the object having increased density. A further aspect may also include applying a non-linear function to the resultant acoustic wave field to deemphasize portions of the resultant acoustic wave field that have bypassed the object. Although a variety of such functions are contemplated, in one aspect the non-linear function can be a sigmoidal function.

Numerous back propagation techniques are possible, all of which are considered to be within the present scope. In one aspect, for example, back propagating the residual to determine corrections to the model of the object includes applying a minimum gradient support constraint. In another aspect, the method may include determining a gradient of the residual, and adding a portion of the gradient to the residual. In one specific aspect the portion of the gradient is scaled by a scale factor. In another specific aspect the scale factor is a constant. In yet another specific aspect the scale factor is a function of an iteration sequence number. In another aspect, back propagating the residual to determine corrections to the model of the object may include preconditioning the residual. Such preconditioning of the residual may include high-pass filtering the residual. In yet another aspect, back propagating the residual to determine corrections to the model of the object may include constraining the model to preclude negative attenuation. In a further aspect, back propagating the residual to determine corrections to the model of the object may include constraining the model to preclude negative speed.

In another aspect of the present invention, a method of imaging internals of a physical object using acoustic waves is provided. Such a method may include transmitting an acoustic wave field toward the object using a transmit array positioned at a transmit position, receiving a resultant acoustic wave field reflected from or transmitted through the object in response to the acoustic wave field using a receive array positioned at a receive position, determining a predicted resultant acoustic wave field derived from a model of the object, and determining a residual between the predicted resultant acoustic wave field and the resultant acoustic wave field. The method may also include back propagating the residual to determine corrections to the model of the object, varying the transmit position and the receive position, and iterating the preceding steps to successively refine the model of the object over a number of iterations until a predefined condition is reached.

Various configurations for the transmit and receive positions are contemplated, and such may vary depending on the nature of the object and the intended results of a particular procedure. In one aspect, for example, the receive position is at a 180 degree azimuth angle to the transmit position relative to the object. In another aspect, the receive position is at a 90 degree azimuth angle to the transmit position relative to the object. In yet another aspect, varying the transmit position and the receive position comprises moving the transmit position and the receive position over a full 360 degree range of azimuth angles.

In another aspect of the present invention, varying the transmit position and the receive position further includes sequentially moving the transmit position and the receive position through a first range of azimuth angles, and sequentially moving the transmit position and the receive position through a second range of azimuth angles separated from the first range of azimuth angles by a step angle. In a more specific aspect, each of the first range and the second range are between about 5 degrees and about 15 degrees.

In yet another aspect, the method may further include moving the transmit position and the receive position through a first range of azimuth angles comprises stepping the transmit position and the receive position over a plurality of first angular positions, and moving the transmit position and the receive position through a second range of azimuth angles comprises stepping the transmit position and the receive position over a plurality of second angular positions. In a more specific aspect, the plurality of first angular positions are separated in azimuth angle by between about 0.5 degrees and about 5 degrees, and the plurality of second angular positions are separated in azimuth angle by between about 0.5 degrees and about 5 degrees. In another more specific aspect, the step angle is within the range of about 15 degrees and about 165 degrees. In yet another more specific aspect, the method may include generating a random or pseudo random step angle.

Additional features and advantages of the invention will be apparent from the detailed description which follows, taken in conjunction with the accompanying drawings, which together illustrate, by way of example, features of the invention.

DEFINITIONS OF KEY TERMS

Figure 1:
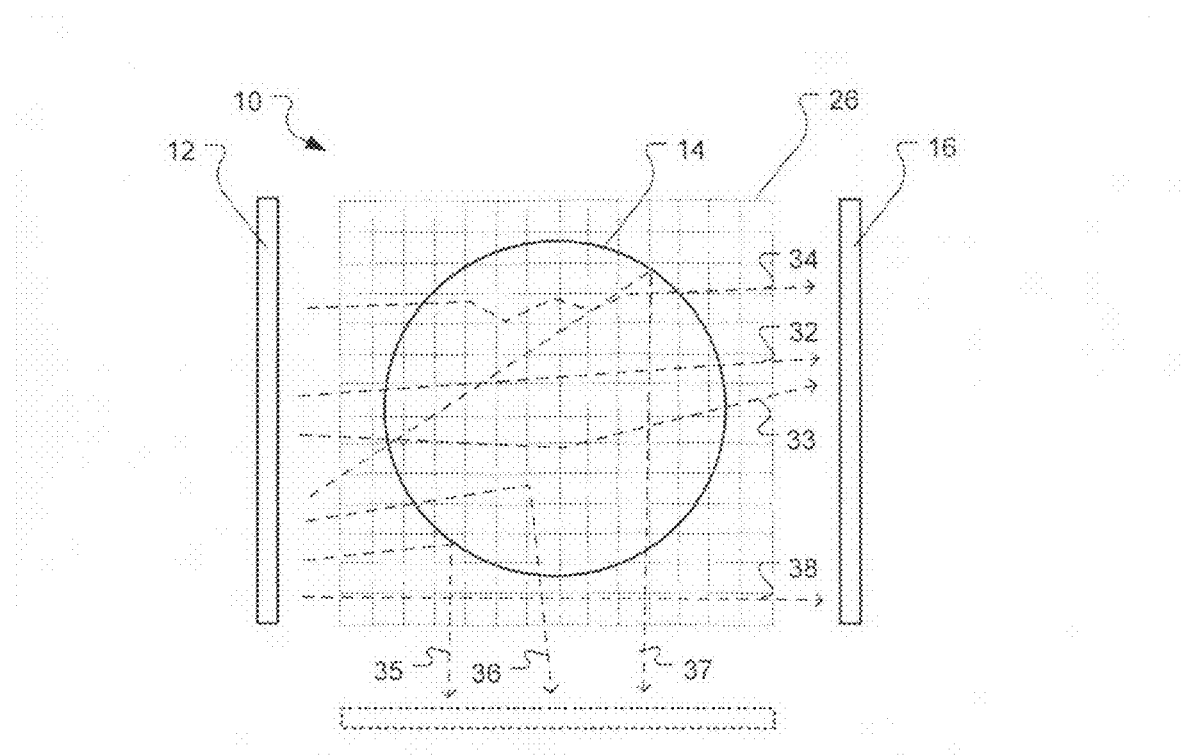
FIG. 1 is a schematic illustration of an acoustic imaging data acquisition subsystem in accordance with an embodiment of the present invention.

As used herein, the singular forms "a," "an," and "the" include plural referents unless the context clearly dictates otherwise. Thus, for example, reference to "a transmitter" includes reference to one or more transmitters.

As is used herein, the term "forward problem" refers to a predictive construction of a resultant acoustic wave field. More particularly, it may be referred to as the forward scattering problem when the resultant acoustic wave field is primarily transmitted through the object, and it may be referred to as the reverse scattering (or back scattering) problem when the resultant acoustic wave field is primarily reflected off the object.

As is used herein, the terms "backward problem," "backward scattering," "inverse problem," and "inverse scattering" refer to corrections to the model of an object that are subsequently made by back propagating the residual between the predicted resultant acoustic wave field and the actual resultant acoustic wave field. Such back propagation is performed taking into account the propagation characteristics of the acoustic wave and the model of the object.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint. Additionally, the term "about" means that dimensions, sizes, parameters, shapes and other quantities and characteristics are not and need not be exact, but may be approximated and/or larger or smaller, as desired, reflecting tolerances, conversion factors, rounding off, measurement error and the like and other factors known to those of skill in the art.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually. This same principle applies to ranges reciting only one numerical value as a minimum or a maximum. Furthermore, such an interpretation should apply regardless of the breadth of the range or the characteristics being described.

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

DETAILED DESCRIPTION

The present invention provides techniques for utilizing acoustic wave fields to image internal structures of physical objects. In one aspect, for example, a method of imaging internals of a physical object using acoustic waves may include transmitting an acoustic wave field toward the object, receiving a resultant acoustic wave field with a receiver, wherein the resultant acoustic wave field is in response to the transmitted acoustic wave field reflected from or transmitted through the object, and determining a predicted resultant acoustic wave field derived from a model of the object. The method may further include determining a residual between the predicted resultant acoustic wave field and the resultant acoustic wave field, and back propagating the residual to determine corrections to the model of the object. Additional aspects may include iterating the steps of transmitting an acoustic wave field, receiving a resultant acoustic wave field, determining a predicted resultant acoustic wave field, determining a residual, and back propagating the residual in order to successively refine the model of the object over a number of iterations until a predefined condition is reached.

A variety of methods are contemplated to image the object as described. In one aspect, for example, a predicted resultant acoustic wave field can be constructed based on a model of the object. Such a predictive construction of the resultant acoustic wave field is referred to as the forward problem. More particularly, it may be referred to as the forward scattering problem when the resultant acoustic wave field is primarily transmitted through the object, and it may be referred to as the reverse scattering (or back scattering) problem when the resultant acoustic wave field is primarily reflected off the object. Various techniques of providing an initial model of the object can be used, as will be described in further detail below. A residual between the predicted resultant acoustic wave field and the actual resultant acoustic wave field is then determined. If the model of the object is a perfect representation of the object, the residual will be zero. In practice this rarely if ever occurs, and the residual will have some finite value(s). Depending on the complexity of the receiver, the residual may be a one-dimensional function (e.g. for a single row of receive transducers), a two-dimensional function (e.g. for a multiple rows of receive transducers), or even a three-dimensional function (e.g. for a complex receiver array with, for example, beam steering, or the like).

Corrections to the model of the object are subsequently made by back propagating the residual between the predicted resultant acoustic wave field and the actual resultant acoustic wave field. The back propagation is performed taking into account the propagation characteristics of the acoustic wave and the model of the object. This can also referred to as inverse scattering or the backward problem.

Various techniques for solving the forward and backward problem which can be applied to aspects of the present invention are provided by the inventors' previously published patents and applications, including U.S. Pat. Nos. 4,662,222; 5,339,282; 5,588,032; 6,005,916; 6,587,540; 6,636,584 and pending U.S. Patent Application Publication Numbers 20040034307; 20060084859; 20060287596; and 20060293597, each of which are hereby incorporated by reference.

Improvements to the model of the object can thus be made by iteratively repeating the process of transmitting an acoustic wave field, receiving a resultant acoustic wave field, determining a predicted resultant acoustic wave field, determining a residual, and back propagating the residual to determine corrections to the model. Such a process can repeat for a number of iterations until a predefined condition is reached. For example, the predefined condition can include the magnitude of the residual being less than a predefined criterion. As a more specific example, the peak magnitude, mean-square error magnitude, or the like may be determined for the residual and compared to a threshold. When the magnitude is less than the threshold, iteration can be concluded. As another example, the predefined condition can include a change in the residual between iterations that is less than a predefined value. As yet another example, the predefined condition can include a rate of change in the residual between iterations that is less than a predefined value. It has been discovered experimentally that a "knee" tends to appear in the residual for which the second-derivative of the residual has dropped to a small value, and that iteration after this point tends to provide little improvement in the image quality.

Between iterations, various parameters may be altered, including for example, the frequency of the acoustic wave, the azimuth position of the transmitter, the azimuth position of the receiver, the elevation of the transmitter, the elevation of the receiver, and the like. As a particular example, iterations may be performed wherein the frequency of the acoustic wave is stepped over a plurality of predetermined frequency values. Use of multiple frequency values can help to improve the quality of the image produced as it helps to resolve ambiguities. It should be noted that any frequency or frequencies beneficial for imaging an object are considered to be within the scope of the present invention. In one aspect, however, the acoustic wave field has a frequency of from about 10 kHz to about 5 MHz.

The model of the object may be defined as a plurality of points on a computational grid. For example, FIG. 1 illustrates a rectangular two-dimensional computational grid 26. For three-dimensional imaging, a three-dimensional computational grid may be used. For example, multiple two-dimensional planar slices at different elevations can be used to build a three-dimensional volume model of the object. As one non-limiting example, the grid may be about 250 by 250 pixels for a two-dimensional slice, and provide about 250 pixels in the third dimension. In one aspect, pixels may correspond to a physical distance of about 1 mm. Although in some aspects a regular, rectangular-coordinate computation grid may be efficient for performing the imaging calculations, in other aspects the computation grid can be irregular or non-rectangular with appropriate adjustments to the wave equations used during the forward and backward problem. At should also be noted that a "stepping size" in the marching direction can vary within the algorithm.

Furthermore, different approximations are considered to the standard wave or Helmholtz equation. For example, in one aspect a marching method may be utilized. In such a case different propagators move the total calculated field from one set of grid points to another set of grid points. In addition to various aspects described herein, in another aspect a coupled set of propagators can be used that result in a better approximation to the Helmholtz equation at a higher computational cost. Additionally, a variety of propagators are contemplated, including, without limitation, Fast Fourier Transforms, direct convolutions, short convolutions, Winograd algorithms, Chinese Remainder Theorem-base algorithms, and finite difference implementations of Split Step Fourier methods.

It may also be useful to utilize techniques to absorb boundary conditions to improve the resolution of the imaging system. The wave propagation in the forward direction can be more accurately modeled by absorbing boundary conditions. For example, in the Fast Fourier Transform or the finite difference based implementation it may be useful to construct appropriate boundary conditions or a wide enough numerical grid on which the numerical calculations are carried out to avoid physically unrealistic signals from an artificially truncated grid. Such appropriate boundary conditions are useful because the numerical grid is, by definition, finite in size, and is therefore truncated in space at some point.

In another aspect, a "rescattering of the total field" can be implemented to partially incorporate the backscattered energy in a more realistic manner than what can be accomplished by a strict marching method. In one specific aspect, such a method may incorporate the use of numerical Green's functions, which are familiar to those of ordinary skill in the art. In another specific aspect, half of the Green's function may be used. In such a method, only the forward propagating part of the Green's function is used in the construction of the total field.

Returning to the computational grid, each point or pixel of the grid may include parameters describing the object characteristics, including for example, a speed parameter, an attenuation parameter, or both. Speed refers the to the propagation velocity of the acoustic wave, including sonic and ultrasonic speeds. The speed of the acoustic wave field will thus change depending on the structural makeup of the material through which it is propagating. As such, the disparate internal makeup of an object will cause portions of the wave field to be propagated at a different speed as compared to other portions of the wave field. Such differential speed variations can thus be indicative of specific internal structures. In addition to speed, attenuation can also be utilized to visualize internal structures within an object.

Attenuation is the reduction of amplitude of the acoustic wave field as it propagates. The structural makeup of a material affects the degree of attenuation that a wave field experiences as it propagates through the material. The disparate internal makeup of an object will cause portions of the wave field to attenuate to a different degree as compared to other portions of the wave field. As with speed variations, such differential attenuation can be indicative of specific internal structures and can be utilized to visualize such structures within the object.

Figure 2:
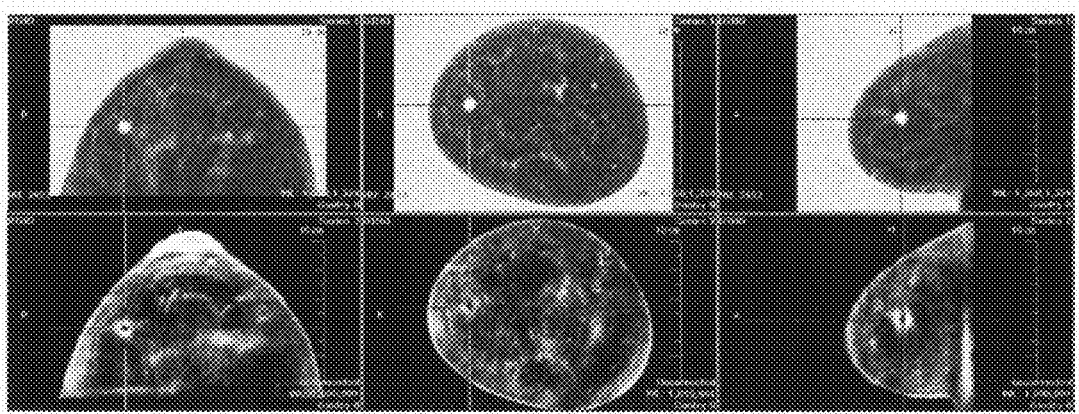
FIG. 2 is an image of a breast scanned in accordance with another embodiment of the present invention.

Accordingly, in one aspect a speed image may be constructed using primarily or solely speed parameters. In another aspect, an attenuation image may be constructed using primarily or solely attenuation parameters. In yet another aspect, a combined image may be constructed using both speed and attenuation parameters. FIG. 2 shows acoustic wave field images obtained of a human breast. The top row shows speed images of different views of the same breast. The bottom row shows attenuation images of different views of the same breast. The middle row shows a combined image using both speed and attenuation parameters to construct the image.

Figure 3:
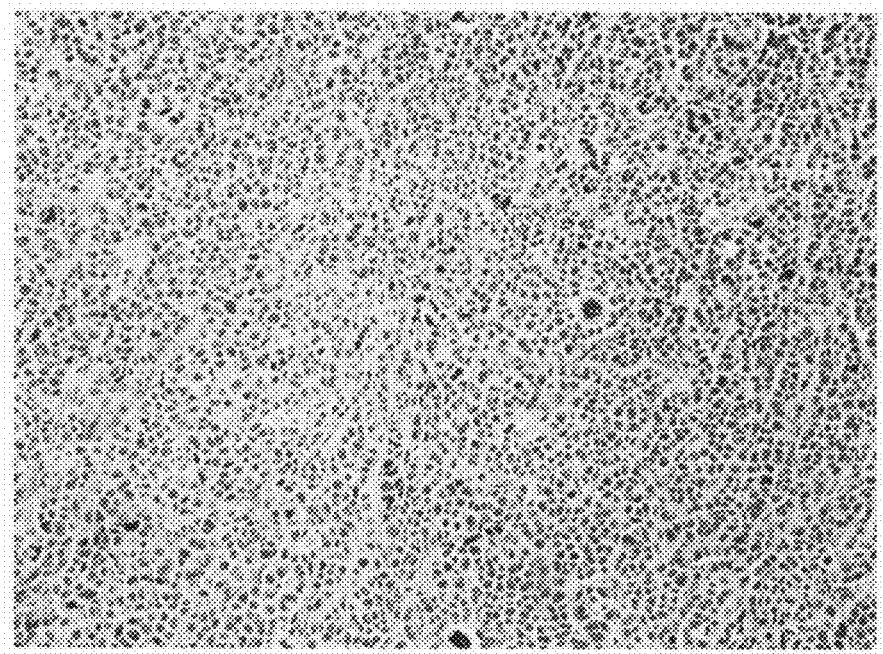
FIG. 3 is an image of a stained slice of tissue in accordance with yet another embodiment of the present invention.
Figure 4:
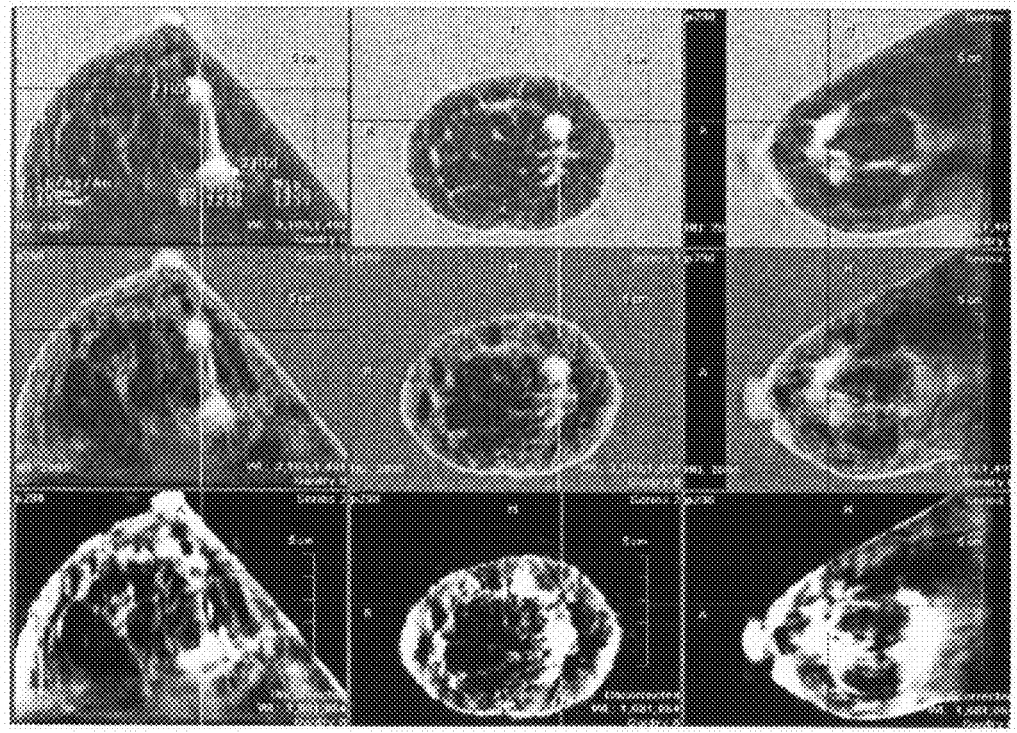
FIG. 4 is an image of a breast scanned in accordance with a further embodiment of the present invention.

In one aspect of the present invention, the imaging techniques described can be beneficial in the screening for breast cancer and other related breast conditions. Many tumors and growths, particularly those of a malignant or pre-malignant nature, have a higher proportion of nuclear material in cells as compared to normal tissue structures. As can be seen in FIG. 3, a histologtical tissue preparation of an excised lobular carcinoma shows a high abundance of stained nuclear material. This stained nuclear material is shown in FIG. 3 as the darker spots throughout the entire tissue. The higher proportions of such material may affect the speed and/or attenuation of acoustic waves moving through the tissue, and thus can be imaged accordingly. For example, FIG. 4 shows acoustic wave field images obtained of a human breast having a malignant growth. The top row shows speed images of different views of the same breast. The growth in the image is displayed as a white spot. The bottom row shows attenuation images of different views of the same breast. The growth in the image displayed as a black spot surrounded by a lighter halo. The spots seen in these images are presumably due to speed and/or attenuation changes facilitated by the structural differences of the growth as compared to normal breast tissue, possibly including the higher abundance of nuclear material.

In forming an object model using both speed and attenuation parameters, the speed parameters, attenuation parameters, or both may be updated during each iteration. Accordingly, during any iteration either one of the speed image or the attenuation image may be held constant while the other one is updated. In general, because the affects on propagation of the speed and attenuation are different, solving the reverse problem is somewhat different for each. For example, attenuation tends to be additive, resulting in a relatively noisy, low resolution image. In contrast, the speed tends to be multiplicative, resulting in high resolution images slightly more prone to artifacts. Accordingly, in some aspects better performance may be obtained by forming a speed image first, then holding speed fixed while improving the attenuation image.

It will be appreciated that the image resolution that can be obtained from the object model is a function of the frequency of the acoustic wave field. Accordingly, the resolution of the computation grid may be varied as a function of acoustic frequency. For example, for lower frequencies, lower resolution is provided, which in turn can be represented by a lower resolution or, in other words, a sub-sampled subset of points from a higher resolution computation grid.

Accordingly, improved computation efficiency can be facilitated by taking advantage of the foregoing resolution relationship. Initial iterations can utilize a low resolution grid and a lower acoustic frequency, thus resulting in a reduced amount of data processing that must be performed. These initial low resolution images can then be improved in later images by utilizing higher acoustic frequencies and, therefore, a high resolution grid. For example, a low resolution grid can utilize a sub-sampled subset of points that are then interpolated to initialize a higher resolution grid. As the iterations are performed, the number of points or pixels used can be increased until the entire computation grid is utilized during later iterations.

As has been described, various techniques for initializing a model of the object can be implemented. For example, the object model can be initialized with a predetermined set of parameters representative of a typical specimen or nominal object. Of course, when imaging objects of varying shapes and sizes, such as human body parts, other approaches may provide a better starting estimate. For example, the model of the object can be initialized using a transmission image or a reflection image. As one non-limiting example, transmission image initialization can be performed by using a time of flight technique. For such a technique it is assumed that there is no refraction or scattering, and that the transmitted acoustic wave field propagates in a direct line from the transmitter to the receiver. The time delay between the transmitted acoustic wave field and the received acoustic wave field thus defines a speed distribution used to initialize the object model. As another non-limiting example, reflection image initialization can be performed by using a reflected acoustic wave technique. Speed parameters can be initialized for the object model based on the transmission time delay or echo time delay between the transmitted acoustic wave field and the received acoustic wave field. In another aspect, attenuation parameters can be initialized for the object model based on attenuation between the acoustic wave field and the resultant acoustic wave field.

Generally a more accurate initialization of the object model results in fewer artifacts appearing in the final images produced by the iteration. In some aspects it may be helpful, however, to blur the initial object model. For example, the reflection image initialization may be performed at a high frequency which provides relatively high resolution. When performing the forward scattering iteration, however, initial improvement of the model may be performed using lower frequencies and thus lower resolution. Under such conditions, therefore, it is helpful to blur the object model by performing, for example, a low pass filtering operation over the computation grid.

One challenge in performing the backward problem can include a high dynamic range variation as a result of differences between acoustic wave energy propagation through the object (e.g. lines 32-34 in FIG. 1) and acoustic wave energy that bypasses the object (e.g., traveling directly from the transmitter to the receiver and bypassing the edge of the object, as shown by line 38 in FIG. 1). Accordingly, various approaches can be used to reduce the dynamic range.

One approach can include modifying the transmitted acoustic wave field so as to reduce field intensity in directions where the acoustic wave field does not pass through the object before reaching the receiver relative to the field intensity in directions where the acoustic wave field does pass through the object before reaching the receiver. In one aspect, for example, a rectangular shaping function can be used, whereby the field intensity can be set to a minimum value at outer portions of the array near the edges of the object and to a maximum value at inner portions of the array near the center of the object. In another aspect, a shaping function may be a non-linear function to more closely match the characteristics of the object and thus further compensate for attenuation through the object. In addition to differentiating between portions of the acoustic wave field that pass through the object vs. portions of the acoustic wave field that don't, it can also beneficial to tailor or "shade" the transmitted acoustic wave field in a manner that reflects the thickness or the density changes of different portions of the object. As a specific example, attenuation generally increases with the thickness of the object, and as such the transmitted acoustic wave can be tailored or filtered to compensate for thickness. Thus for a round object a half-sine or half-sine-squared pulse may provide good reduction in dynamic range presented to the receiver. As another specific example, a sigmoidal function can be used.

In another aspect, a non-linear function may be applied to the resultant acoustic wave field to deemphasize portions of the resultant acoustic wave field that have bypassed the object or that have passed through portions of the object that have a decreased thickness as compared to other portions of the object. This approach has the benefit of avoiding the added complexity of shaping the transmitted acoustic wave field intensity and avoids a high dynamic range at the transmitter. On the other hand, the dynamic range of the receiver may still be high, although the non-linear function can help to reduce the dynamic range of digitized data. As with tailoring the transmitted acoustic wave field, the non-linear function applied to the resultant acoustic wave field can be a variety of functions, including, without limitation, sigmoidal functions, half-sine-squared functions, half-sine functions, and combinations thereof.

Additional improvements in performance can be obtained by dividing the resultant acoustic wave field by an incident wave field to help to calibrate out characteristics of the receiver. The incident wave field can, for example, be determined by predicting the incident wave field received at the receiver in response to the transmitted wave field when the object is not present. As an alternative to predicting the reference wave field, the incident wave field can be determined by transmitting an acoustic wave field toward the receiver when the object is not present and receiving an incident wave field at the receiver.

In many cases, solving the reverse problem is quite complex. Moreover, because the solution to the reverse problem may not be unique, it is possible to generate artifacts in the images that are produced. A variety of approaches can help to minimize the generation of such artifacts. For example, iterating over multiple acoustic frequencies can help to resolve ambiguities in the reverse problem. As another example, iterating over multiple angles can also help to improve resolution, as is described further below.

Various constraints can also be applied to the reverse problem to help ensure an accurate solution. For example, when back propagating the residual to determine corrections to the object model, it can be helpful to constrain the solution so that negative attenuation and negative speed are precluded. Additionally, when back propagating the residual, in one aspect a minimum gradient support constraint can be applied to help sharpen edges while reducing artifacts. In another aspect, a total variation constraint may be utilized. Total variation is a mathematical term describing the integral of the magnitude of the gradient over the entire or substantially the entire space. It is a measure similar to arc-length. In one specific aspect, a Tikhonov regularization scheme may be used as a form of regularization/constraint. It should be noted that such a scheme is familiar to one of ordinary skill in the art.

As another example, it can be useful to determine the frequency gradient of the residual, and then add a portion of the frequency gradient to the residual. For example, the gradient of the residual can be determined, a magnitude square of the gradient formed, and then a scale factor applied. The scale factor may be a constant or the scale factor may be a variable. In one specific example of such a variable the scale factor may vary as a function of the iteration sequence number, thus reducing in value as the iteration sequence number increases. This can help to speed convergence of the backward problem.

Before back propagating the residual, it can also be helpful to precondition the residual. Various preconditioning approaches can be used, including for example applying a filter operation to the residual. In one aspect, for example, a the residual may be high-pass filtered. In another aspect, a Shepp-Logan like filter operation may be applied to the data (both predicted and measured data). As such, one filter may described as a 'wedge-filter with a roll-off at high frequencies', or as a 'windowed wedge-filter', or as a 'windowed standard CT filter'. In some aspects it may be beneficial to apply the square root of the filter to the data, since the filter may be applied again when the Hermitian adjoint is applied to the residual in the back-propagation process. It should be noted that any filter would be considered to be within the scope of the present invention that can be applied to the data and algorithm in a consistent manner to acts as a preconditioner, thus increasing the iterative algorithm's convergence properties.

FIG. 1 provides a schematic illustration of an acoustic imaging data acquisition subsystem accordance with an embodiment of the present invention. The subsystem 10 includes a transmitter 12, for example, an array of ultrasonic transducers, for transmitting an acoustic wave field toward an object 14. A receiver 16, for example, an array of ultrasonic transducers, can receive a resultant acoustic wave field reflected from or transmitted through the object. The object may be, for example, a body part, such as a human breast. Acoustic waves transmitted by the transmitter 12 propagate toward into the object 14, producing reflected, refracted, scattered, and transmitted components which may be received by the receiver 16. While the transmitter 12 and receiver 16 are shown here as being generally linear, it should be appreciated that the transmitter and receiver can be arrays of transducers arranged in other geometries, including for example, shapes that approximate the shape of the object to minimize transmission of acoustic waves into areas around the object.

The receiver 16 may be positioned as shown in FIG. 1 at a 180 degree azimuth angle relative to the transmitter 12 to receive primarily transmitted and scattered components. Azimuth is defined as being in the plane of the drawing of FIG. 1, and elevation refers to movement out of the plane of FIG. 1. As another example, the receiver may be positioned at a 90 degree azimuth angle relative to the transmitter 12, for example as shown in alternate position 16', to receive primarily scattered (forward scattered and reflected scattered) components. As yet another example, the receiver may be positioned in the same location as the transmitter 12, for example, by interleaving transmitter transducers and receiver transducers. As yet another example, transducers can be used for both the transmit and receive function, transmitting a transmit pulse and then quickly switching into a receive mode.

Figure 5:
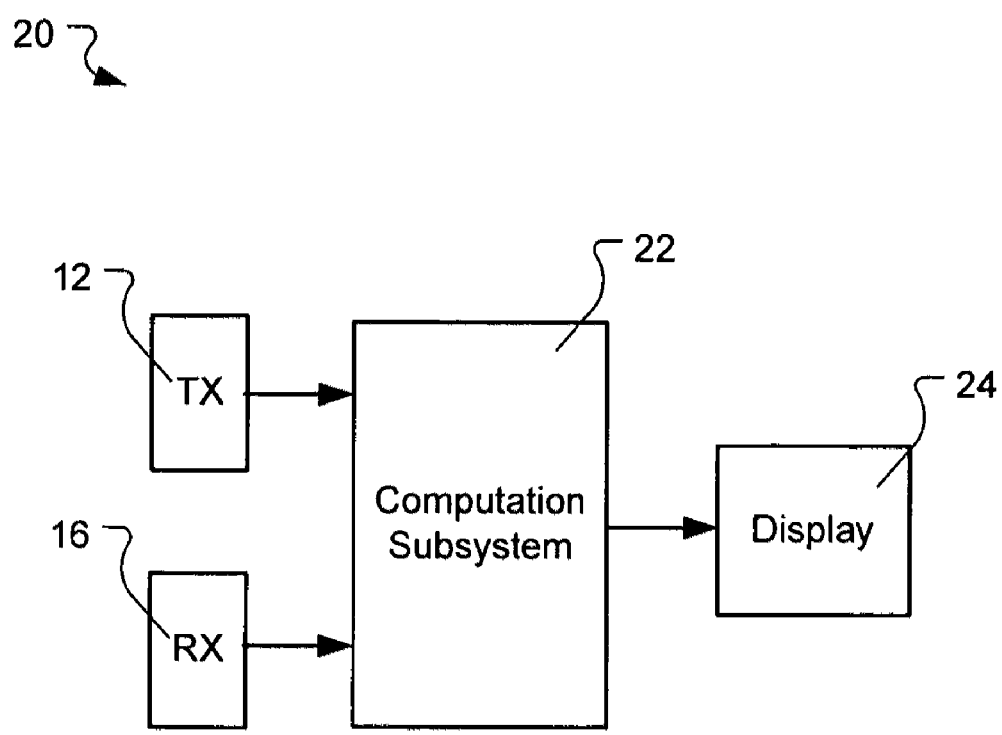
FIG. 5 is a schematic block diagram of an acoustic imaging system in accordance with yet a further embodiment of the present invention.

FIG. 5 illustrates a block diagram illustration of an acoustic imaging system 20 in accordance with an embodiment of the present invention. The transmitter 12 and receiver 16 are coupled to a computation subsystem 22, which performs the computation to generate an image of the object 14 (FIG. 1). The resultant acoustic wave field received by the receiver is digitized for processing by the computation subsystem.

The basic process for imaging is as follows. An acoustic wave field is transmitted toward the object 14 using the transmitter 12. A resultant acoustic wave field is produced in response to the transmitted acoustic wave field and is received using the receiver 16. The resultant acoustic wave field may be substantially transmitted through the object, substantially reflected from the object, or a combination of both. Reference to transmitted through the object is meant to include wave field components which are propagated straight from the transmitter to the receiver (e.g., line 32 on FIG. 1), components which are refracted (line 33), and components which are scattered (line 34). By reflected from the object is meant to include wave field components which are reflected from an exterior surface of the object (and thus never enter the object) (line 35), components which are reflected from internal features of the object (and thus traverse through a portion of the object) (line 36), and components which are reflected from internal surfaces of the object (line 37).

It should be appreciated that not all received components will necessary be transmitted or reflected by the object 14, as paths may be present within the acoustic imaging data acquisition subsystem 10 that allow for direct propagation from the transmitter 12 to the receiver 16, or allow for reflections from portions of the subsystem. It will also be appreciated that the resultant acoustic wave field is thus a complex function of the transmitted acoustic wave field parameters, transmitter and receiver device characteristics, characteristics of any medium (e.g., water, oil, gel, etc.) between the object and the transmitter and receiver, and the geometry of the acoustic imaging data acquisition subsystem. Undesired reflections may be minimized, for example, by using absorbing materials and attenuating medium within the system.

Based on the model of the object, an image can thus be produced and output from the acoustic imaging system 20. For example, the image may be displayed on a display 24. As another example, the image may be printed, for example with a printer (not shown). As yet another example, the image may be electronically transmitted to a data processing system, for example a computer work station, a data archival system, a data transmission system, or the like, or combinations thereof. A data processing system may allow display of the image at a remote location or storage and later retrieval of the image.

Figure 6:
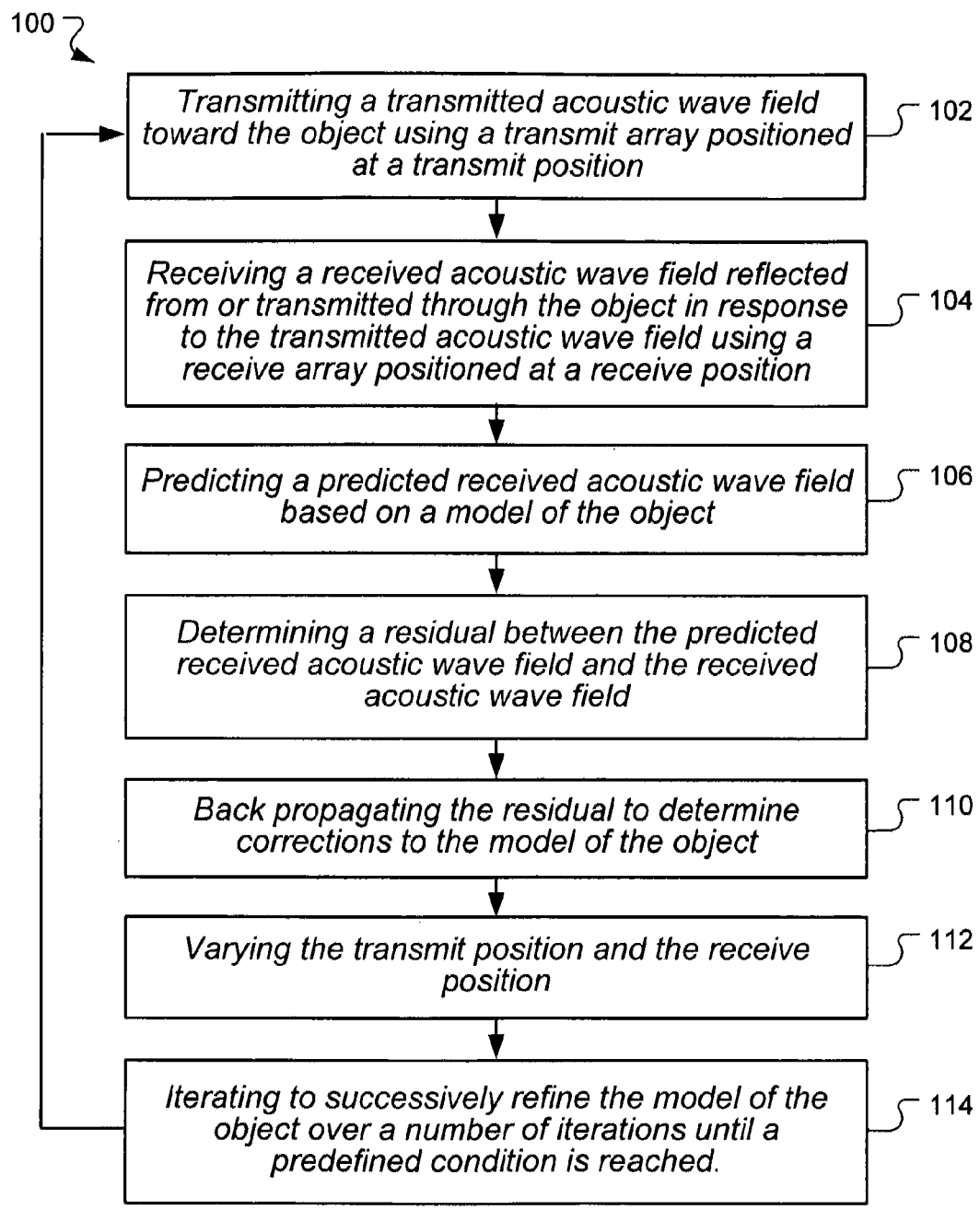
FIG. 6 is a flow chart of a method of imaging the internals of a physical object using acoustic waves in accordance with yet another embodiment of the present invention.

FIG. 6 illustrates a flow chart of one method 100 of imaging the internals of a physical object using acoustic waves in accordance with an embodiment of the present invention. The method includes transmitting 102 an acoustic wave field from a transmitter at a transmit position, receiving 104 a resultant acoustic wave in response to the transmitted acoustic wave by a receiver at a receive position, predicting 106 a predicted resultant acoustic wave based on a model of the object, determining 108 a residual, and back propagating 110 the residual to determine corrections to the model. The previous steps, referred to subsequently as processing a view, have been described in further detail above. The method also includes varying 112 the transmit position and the receive position. The method includes iterating 114 the above steps to successively refine the model of the object until a predefined condition as reached. Various predefined conditions are described above.

Turning to the varying 112 of the transmit position and receive position, the positions of the transmitter 12 (FIG. 1) and the receiver 16 may be moveable around the object. For example, in one aspect the transmitter and receiver may be mounted on a yoke at positions separated by 180 degrees in azimuth and rotatable about the object. In another aspect receivers may also be mounted on the yoke at other angles, for example, at 90 degrees azimuth relative to the transmitter. As another example, the transmitter and receiver may be mounted separately, to allow control of their position independently. For example, the transmitter and receiver may be movable in increments of 2 degrees around the object over a range of 360 degrees.

The imaging method can also include processing a group of views to improve the object model. It should be noted that in one aspect group views are intended to be used simultaneously. In other words, in one iteration of an algorithm a group of views are simultaneously taken into account. It will be appreciated that views from different angles can help to resolve internal object features. Of course, when limited processing time is available, a tradeoff exists between how much iteration is performed at each view, and how many different views are used. For example, performing a large number of iterations at one view may be of limited value since some features could be hidden or shaded by other features in front. Conversely, using many views with only a few iterations may result in many artifacts, as the solution is not allowed to adequately converge.

In one aspect, for example, a group of views covering a range of about 5 to about 15 degrees, or more particularly about 12 degrees in azimuth, may provide good performance. In another aspect, the transmit position and the receive position can be moved through a first range of azimuth angles, and the views processed for each azimuth angle. Within each range of angles, individual views can be stepped through various azimuth angles separated between about 0.5 and about 5 degrees, or more particularly, about 2 degrees. The transmit position and the receive position can then be moved through a second range of azimuth angles, and the views processed. Better performance is obtained when the ranges are separated so they are somewhat orthogonal. For example, the first range and the second range can be separated from each other by about a step angle between about 15 degrees and about 165 degrees. The step angle can be a predetermined sequence, or can be selected randomly or pseudorandomly. It has been observed using the above techniques that resolution of about 1.7 mm can be obtained in the horizontal dimension (plane of rotation of the transmitter and receiver) and about 3 mm in the vertical dimension.

It is to be understood that the above-referenced arrangements are only illustrative of the application for the principles of the present invention. Numerous modifications and alternative arrangements can be devised without departing from the spirit and scope of the present invention. While the present invention has been shown in the drawings and fully described above with particularity and detail in connection with what is presently deemed to be the most practical and preferred embodiment(s) of the invention, it will be apparent to those of ordinary skill in the art that numerous modifications can be made without departing from the principles and concepts of the invention as set forth herein.

What is claimed is:

1. A method of imaging internals of a physical object using acoustic waves, comprising:
   a) transmitting an acoustic wave field toward the object;
   b) receiving a resultant acoustic wave field with a receiver, wherein the resultant acoustic wave field is in response to the transmitted acoustic wave field reflected from or transmitted through the object;
   c) determining a predicted resultant acoustic wave field derived from a model of the object;
   d) determining a residual between the predicted resultant acoustic wave field and the resultant acoustic wave field;
   e) back propagating the residual to determine corrections to the model of the object, wherein back propagating the residual comprises either holding the speed parameters constant while updating the attenuation parameters or holding the attenuation parameters constant while updating the speed parameters;
   f) refining the model with the corrections to the model; and
   g) iterating steps (a) through (f) to successively refine the model of the object over a number of iterations until a predefined condition is reached.

2. The method of claim 1, wherein the object is a body part.

3. The method of claim 2, wherein the object is a human breast.

4. The method of claim 1, wherein the acoustic wave field has a frequency of between about 10 kHz and about 5 MHz.

5. The method of claim 4, wherein the frequency of the acoustic wave is changed at least once between iterations of steps (a) through (e).

6. The method of claim 4, wherein the frequency of the acoustic wave is stepped over a plurality of predetermined frequency values.

7. The method of claim 1, further comprising outputting an image derived from the model of the object.

8. The method of claim 1, wherein the predefined condition comprises a magnitude of the residual being less than a predefined criterion.

9. The method of claim 1, wherein the predefined condition comprises a change in the residual between iterations that is less than a predefined criterion.

10. The method of claim 1, wherein the predefined condition comprises a rate of change in the residual between iterations that is less than a predefined criterion.

11. The method of claim 1, further comprising:
receiving the resultant acoustic wave field transmitted through the object; and
initializing the model of the object based on the resultant acoustic wave field.

12. The method of claim 11, wherein initializing the model of the object comprises:
defining a plurality of points on a computation grid to represent the object; and
initializing a speed parameter associated with each of the plurality of points based on transmission time delay between the transmitted acoustic wave field and the resultant acoustic wave field.

13. The method of claim 11, wherein initializing the model of the object comprises:
defining a plurality of points on a computation grid to represent the object; and
initializing an attenuation parameter associated with each of the plurality of points based on attenuation between the transmitted acoustic wave field and the resultant acoustic wave field.

14. The method of claim 1, comprising:
receiving the resultant acoustic wave field reflected from the object; and
initializing the model of the object based on the resultant acoustic wave field.

15. The method of claim 14, wherein initializing the model of the object comprises:
defining a plurality of points on a computation grid to represent the object; and
initializing a speed parameter associated with each of the plurality of points based on echo time delay between the acoustic wave field and the resultant acoustic wave field.

16. The method of claim 15, further comprising blurring the model of the object.

17. The method of claim 16, wherein blurring the model of the object comprises performing a low pass filtering operation over the computation grid.

18. The method of claim 1, wherein the model of the object comprises a plurality of points on a computational grid.

19. The method of claim 18, wherein each of the plurality of points comprises a speed parameter to define a speed image.

20. The method of claim 18, wherein each of the plurality of points comprises an attenuation parameter to define an attenuation image.

21. The method of claim 18, wherein each of the plurality of points comprises a speed parameter to define a speed image and an attenuation parameter to define an attenuation image.

22. The method of claim 18, wherein the computational grid comprises a rectangular arrangement of the plurality of points.

23. The method of claim 18, wherein the computational grid comprises a rectangular arrangement of the plurality of points in a two-dimensional plane.

24. The method of claim 18, wherein the computational grid comprises a rectangular arrangement of the plurality of points in a three-dimensional space.

25. The method of claim 18, wherein the resolution of the computational grid varies as a function of the acoustic wave frequency.

26. The method of claim 18, wherein back propagating the residual to determine corrections to the model of the object further includes:
using a sub-sampled subset of points in the computational grid during a first subset of a number of iterations performed at a first acoustic wave frequency;
interpolating the sub-sampled subset of the computation grid to initialize points not in the sub-sampled subset; and
using the entire computational grid during a second subset of the iterations performed at a second acoustic wave frequency.

27. The method of claim 1, further comprising
determining an incident wave field when the object is not present; and
dividing the resultant acoustic wave field by the incident wave field.

28. The method of claim 27, wherein determining the incident wave field further includes:
transmitting an acoustic wave field toward the receiver when the object is not present; and
receiving an incident acoustic wave field at the receiver in response to the acoustic wave field.

29. The method of claim 27, wherein determining an incident wave field further includes predicting an incident acoustic wave field received at the receiver in response to the acoustic wave field when the object is not present.

30. The method of claim 1, further comprising
tailoring the acoustic wave field to reduce field intensity in directions where the acoustic wave field does not pass through the object before reaching the receiver relative to field intensity in directions where the acoustic wave field does pass through the object before reaching the receiver.

31. The method of claim 30, wherein tailoring the acoustic wave field further includes tailoring the acoustic wave field to reduce field intensity in directions where the acoustic wave field passes through portions of the object having decreased tissue thickness relative to portions of the object having increased tissue thickness.

32. The method of claim 30, wherein tailoring the acoustic wave field further includes tailoring the acoustic wave field to reduce field intensity in directions where the acoustic wave field passes through portions of the object having reduced density relative to portions of the object having increased density.

33. The method of claim 1, further comprising:
applying a non-linear function to the resultant acoustic wave field to deemphasize portions of the resultant acoustic wave field that have bypassed the object.

34. The method of claim 33, wherein the non-linear function is a sigmoidal function.

35. The method of claim 1, wherein back propagating the residual to determine corrections to the model of the object comprises applying a minimum gradient support constraint.

36. The method of claim 1, further comprising:
determining a frequency gradient of the residual; and
adding a portion of the frequency gradient to the residual.

37. The method of claim 36, wherein the portion of the gradient is scaled by a scale factor.

38. The method of claim 37, wherein the scale factor is a constant.

39. The method of claim 37, wherein the scale factor is a function of an iteration sequence number.

40. The method of claim 1, wherein back propagating the residual to determine corrections to the model of the object comprises preconditioning the residual.

41. The method of claim 40, wherein preconditioning the residual comprises high-pass filtering the residual.

42. The method of claim 1, wherein back propagating the residual to determine corrections to the model of the object comprises constraining the model to preclude negative attenuation.

43. The method of claim 1, wherein back propagating the residual to determine corrections to the model of the object comprises constraining the model to preclude negative speed.

44. A method of imaging internals of a physical object using acoustic waves, comprising:
   a) transmitting an acoustic wave field toward the object using a transmit array positioned at a transmit position;
   b) receiving a resultant acoustic wave field reflected from or transmitted through the object in response to the acoustic wave field using a receive array positioned at a receive position;
   c) determining a predicted resultant acoustic wave field derived from a model of the object;
   d) determining a residual between the predicted resultant acoustic wave field and the resultant acoustic wave field;
   e) back propagating the residual to determine corrections to the model of the object, wherein back propagating the residual comprises either holding the speed parameters constant while updating the attenuation parameters or holding the attenuation parameters constant while updating the speed parameters;
   f) refining the model with the corrections to the model;
   g) varying the transmit position and the receive position; and
   h) iterating steps (a) through (g) to successively refine the model of the object over a number of iterations until a predefined condition is reached.

45. The method of claim 44, wherein the receive position is at a 180 degree azimuth angle to the transmit position relative to the object.

46. The method of claim 44, wherein the receive position is at a 90 degree azimuth angle to the transmit position relative to the object.

47. The method of claim 44, wherein varying the transmit position and the receive position comprises moving the transmit position and the receive position over a full 360 degree range of azimuth angles.

48. The method of claim 44, wherein varying the transmit position and the receive position further includes:
   sequentially moving the transmit position and the receive position through a first range of azimuth angles; and
   sequentially moving the transmit position and the receive position through a second range of azimuth angles separated from the first range of azimuth angles by a step angle.

49. The method of claim 48, wherein each of the first range and the second range are between about 5 degrees and about 15 degrees.

50. The method of claim 48, wherein:
   moving the transmit position and the receive position through a first range of azimuth angles comprises stepping the transmit position and the receive position over a plurality of first angular positions; and
   moving the transmit position and the receive position through a second range of azimuth angles comprises stepping the transmit position and the receive position over a plurality of second angular positions.

51. The method of claim 50 wherein:
   the plurality of first angular positions are separated in azimuth angle by between about 0.5 degrees and about 5 degrees; and
   the plurality of second angular positions are separated in azimuth angle by between about 0.5 degrees and about 5 degrees.

52. The method of claim 48, wherein the step angle is within the range of about 15 degrees and about 165 degrees.

53. The method of claim 48, further comprising generating a random or pseudo random step angle.

* * * * *